(12) United States Patent  
Sharma et al.

(10) Patent No.: US 12,334,224 B2
(45) Date of Patent: Jun. 17, 2025

(54) CARDIOVASCULAR ASSESSMENT OF PATIENTS SUSPECTED OF HAVING COVID-19

(71) Applicant: Siemens Healthineers AG, Forchheim (DE)

(72) Inventors: Puneet Sharma, Princeton Junction, NJ (US); Saikiran Rapaka, Pennington, NJ (US); Ingo Schmuecking, Yardley, PA (US)

(73) Assignee: Siemens Healthineers AG, Forchheim (DE)

( * ) Notice: Subject to any disclaimer, the term of this patent is extended or adjusted under 35 U.S.C. 154(b) by 752 days.

(21) Appl. No.: 16/877,646

(22) Filed: May 19, 2020

(65) Prior Publication Data

US 2021/0319900 A1 Oct. 14, 2021

Related U.S. Application Data

(60) Provisional application No. 63/009,517, filed on Apr. 14, 2020.

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/0205* (2013.01); *A61B 5/4842* (2013.01); *G16H 10/60* (2018.01);
(Continued)

(58) Field of Classification Search
CPC ........ G16H 30/40; G16H 30/20; G16H 50/20; G16H 10/60; G16H 50/70; G16H 40/63;
(Continued)

(56) References Cited

U.S. PATENT DOCUMENTS 7,843,572 B2 11/2010 Tearney et al.
2011/0202486 A1 8/2011 Fung et al.
(Continued)

FOREIGN PATENT DOCUMENTS

CN 101304682 A 11/2008
CN 103493054 A 1/2014
(Continued)

OTHER PUBLICATIONS

Extended European Search Report (EESR) mailed Aug. 27, 2021 in corresponding European patent application No. 21167781.0.
(Continued)

*Primary Examiner* — Ajibola A Akinyemi

(57) ABSTRACT

Systems and methods for assessing cardiovascular disease of a patient are provided. Patient data of the patient is received. The patient data may include one or more input medical images of a chest of the patient, results of an assessment of a lung disease performed based on the one or more input medical images, demographic and clinical data of the patient, and cardiovascular imaging exams of the patient. One or more risk scores are computed for the patient based on the patient data using a trained machine learning based network.

18 Claims, 5 Drawing Sheets

(51) Int. Cl.
*A61B 5/0205* (2006.01)
*G16H 10/60* (2018.01)
*G16H 50/20* (2018.01)
*G16H 50/50* (2018.01)
*G06T 7/00* (2017.01)

(52) U.S. Cl.
CPC ............ *G16H 50/20* (2018.01); *G16H 50/50* (2018.01); *G06T 7/0012* (2013.01); *G06T 2207/20084* (2013.01); *G06T 2207/30061* (2013.01)

(58) Field of Classification Search
CPC ........ G16H 50/30; G16H 50/50; G16H 20/17; G16H 10/20; G16H 15/00; G16H 70/00; G16H 80/00
USPC ......................................................... 382/128
See application file for complete search history.

(56) References Cited

U.S. PATENT DOCUMENTS

| | | | | |
|---|---|---|---|---|
| 2012/0269413 | A1* | 10/2012 | Hautvast | G06T 11/206 382/128 |
| 2015/0192653 | A1* | 7/2015 | Sharif | G06T 11/003 600/420 |
| 2016/0029971 | A1* | 2/2016 | Sachdev | A61B 5/7271 600/529 |
| 2016/0203263 | A1* | 7/2016 | Maier | G16H 30/40 705/2 |
| 2018/0315182 | A1* | 11/2018 | Rapaka | G06T 7/0012 |
| 2020/0353085 | A1* | 11/2020 | Farmer | A61K 47/14 |
| 2021/0287795 | A1* | 9/2021 | Declerck | G16H 30/20 |

FOREIGN PATENT DOCUMENTS

| | | | |
|---|---|---|---|
| CN | 108784655 | A | 11/2018 |
| CN | 110444275 | A | 11/2019 |
| EP | 3404666 | A2 | 11/2018 |
| EP | 3404667 | A1 | 11/2018 |
| EP | 3564963 | A1 | 11/2019 |

OTHER PUBLICATIONS

De Vos, et al: "Automatic machine learning based prediction of cardiovascular events in lung cancer screening data"; Progress in Biomedical Optics and Imaging, SPIE—International Society for Optiocal Engineering, Bellingham, WA, US; vol. 9414, Mar. 20, 2015 (Mar. 20, 2015), pp. 91410D-94140D.

Zheng et al., "COVID-19 and the Cardiovascular System", Nature Reviews Cardiology, May 2020, https://doi.org/10.1038/s41569-020-0360, vol. 17, pp. 259-260.

Shi et al., "Association of Cardiac Injury With Mortality in Hospitalized Patients With COVID-19 in Wuhan, China", JAMA Cardiology, doi:10.1001/jamacardio.2020.0950, published online Mar. 25, 2020, pp. E1-E8.

Guo et al., "Cardiovascular Implications of Fatal Outcomes of Patients With Coronavirus Disease 2019 (COVID-19)", JAMA Cardiology, doi:10.1001/jamacardio.2020.1017, published online Mar. 27, 2020, pp. E1-E8.

De Vos, Bob et al:"Automatic machine learning based prediction of cardiovascular events in lung cancer screening data", SPIE, SPIEDigitallibrary.org/conference-proceedings-of-spie, Dec. 31, 2015; doi: 10.1117/12.2.

Liming Liu et al:; " 基于数据镁掘心血管疾病风险因子发现与早期预警的风险建模研究"; "; Jul. 15, 2017; (English summary enclosed).

Anonymous Yuhui et al: "Temporal Changes of CT Findings in 90 Patients with COVID-19 Pneumonia: A Longitudinal Study I Radiology", Radiology, vol. 296, No. 2, Mar. 19, 2020 (Mar. 19, 2020), pp. E55-E64, XP093188100, us ISSN: 0033-8419, DOI:10.1148/radiol.2020200843 , Retrieved from the Internet: URL:https://pubs.rsna.org/doi/full/10.1148/radiol.2020200843.

Anonymous Agrawal Abhinav et al: "Cardiac manifestations of idiopathic pulmonary fibrosis—PMC", Intractable & Rare Diseases Research, vol. 5, No. 2, Jan. 1, 2016 (Jan. 1, 2016), pp. 70-75, XP093188118, ISSN: 2186-3644, DOI: 10.5582/irdr.2016.01023 , Retrieved from the Internet: URL:https://www.ncbi.nlm.nih.gov/pmc/articles/PMC4869585/.

"Anonymous Steven D. et al: ""The value of computed tomography scanning for the detection of coronary artery disease in patients with idiopathic pulmonary fibrosis—Nathan—2011—Respirology—Wiley Online Library"", Respirology, vol. 16, No. 3, Apr. 1, 2011 (Apr. 1, 2011), pp. 481-486, XP093188132, Hoboken, USA ISSN: 1323-7799, DOI: 10.1111/j.1440-1843.2010.01919.x Retrieved from the Internet: URL:https://onlinelibrary.wiley.com/doi/full/10.1111/j.1440-1843.2010.01919.x".

* cited by examiner

CARDIOVASCULAR ASSESSMENT OF PATIENTS SUSPECTED OF HAVING COVID-19

CROSS-REFERENCE TO RELATED APPLICATIONS

This application claims the benefit of U.S. Provisional Application No. 63/009,517, filed Apr. 14, 2020, the disclosure of which is incorporated herein by reference in its entirety.

TECHNICAL FIELD

The present invention relates generally to a cardiovascular assessment, and in particular to the cardiovascular assessment of patients confirmed as having or suspected of having COVID-19 (coronavirus disease 2019) for patient management.

BACKGROUND

COVID-19 (coronavirus disease 2019) is an infectious disease caused by the severe-acute respiratory symptom coronavirus 2 (SARS-Cov2). Common symptoms of COVID-19 include fever, cough, and difficulty breathing. In the majority of cases, patients infected with COVID-19 experience mild to moderate symptoms that do not require hospitalization. However, in severe cases, COVID-19 can cause pneumonia, severe acute respiratory syndrome, multiple organ failure, and death.

Studies have shown that patients infected with COVID-19 that also have underlying cardiovascular disease are at a higher risk for experiencing severe symptoms of COVID-19. Typically, patients suspected of being infected with COVID-19 receive CT (computed tomography) imaging of the chest for the purpose of assessing the lungs for pneumonia and other pulmonary diseases. However, existing automatic techniques are not able to assess the cardiovascular system of a patient based on such CT imaging, since the CT imaging is primarily performed to assess the lungs of the patient and is not optimized for assessing cardiovascular disease of the patient.

BRIEF SUMMARY OF THE INVENTION

In accordance with one or more embodiments, systems and methods for assessing cardiovascular disease of a patient are provided. Patient data of the patient is received. The patient data may include one or more input medical images of a chest of the patient, results of an assessment of a lung disease performed based on the one or more input medical images, demographic and clinical data of the patient, and cardiovascular imaging exams of the patient. One or more cardiovascular risk scores are computed for the patient based on the patient data using a trained machine learning based network. The patient may be managed based on the one or more cardiovascular risk scores.

In one embodiment, the lung disease may be COVID-19 (coronavirus disease 2019) or another viral pneumonia.

In one embodiment, the one or more input medical images are acquired without a contrast agent and without cardiac gating.

In one embodiment, the one or more risk scores is a metric representing an assessment of a cardiovascular disease and the assessment of the lung disease.

In one embodiment, the patient data includes sensor data of physiological measurements of the patient. The sensor data may be continuously received and the patient may be monitored based on the continuously received sensor data and the cardiovascular assessment.

These and other advantages of the invention will be apparent to those of ordinary skill in the art by reference to the following detailed description and the accompanying drawings.

DETAILED DESCRIPTION

The present invention generally relates to methods and systems for the cardiovascular assessment of patients confirmed as having or suspected of having COVID-19 (coronavirus disease 2019). Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

COVID-19 is an infectious disease that typically presents such respiratory symptoms as fever, cough, and difficulty breathing. Patients with COVID-19 that also have underlying cardiovascular disease have been found to exhibit more severe symptoms of COVID-19 and have worse patient outcomes (including death). Typically, patients suspected of having COVID-19 receive CT (computed tomography) imaging of the chest in order to assess the lungs. The CT imaging is primarily performed for the purpose of assessing the lungs and, therefore, the CT imaging is performed without contrast agent and without cardiac gating, resulting in relatively lower image quality of cardiovascular structures as compared to CT imaging typically used to assess cardiovascular disease. Embodiments described herein provide for a machine learning based system for the cardiovascular assessment of a patient using such CT imaging. Advantageously, the cardiovascular assessment for patients confirmed as having or suspected of having COVID-19 in accordance with embodiments described herein allows for improved patient management decisions and patient stratification, enabling better use of clinical resources and improved patient outcomes.

It should be understood that while embodiments described herein are described with respect to the cardiovascular assessment of patients confirmed as having or suspected of having COVID-19, such embodiments are not so limited. Embodiments may be applied for the cardiovascular assessment of patients confirmed as having or suspected of having any lung disease (e.g., other types of viral pneumonia (e.g., SARS (severe acute respiratory syndrome), MERS (Middle East respiratory syndrome), etc.), bacterial pneumonia, fungal pneumonia, mycoplasma pneumonia, and other types of pneumonia and other types of diseases).

Figure 1:
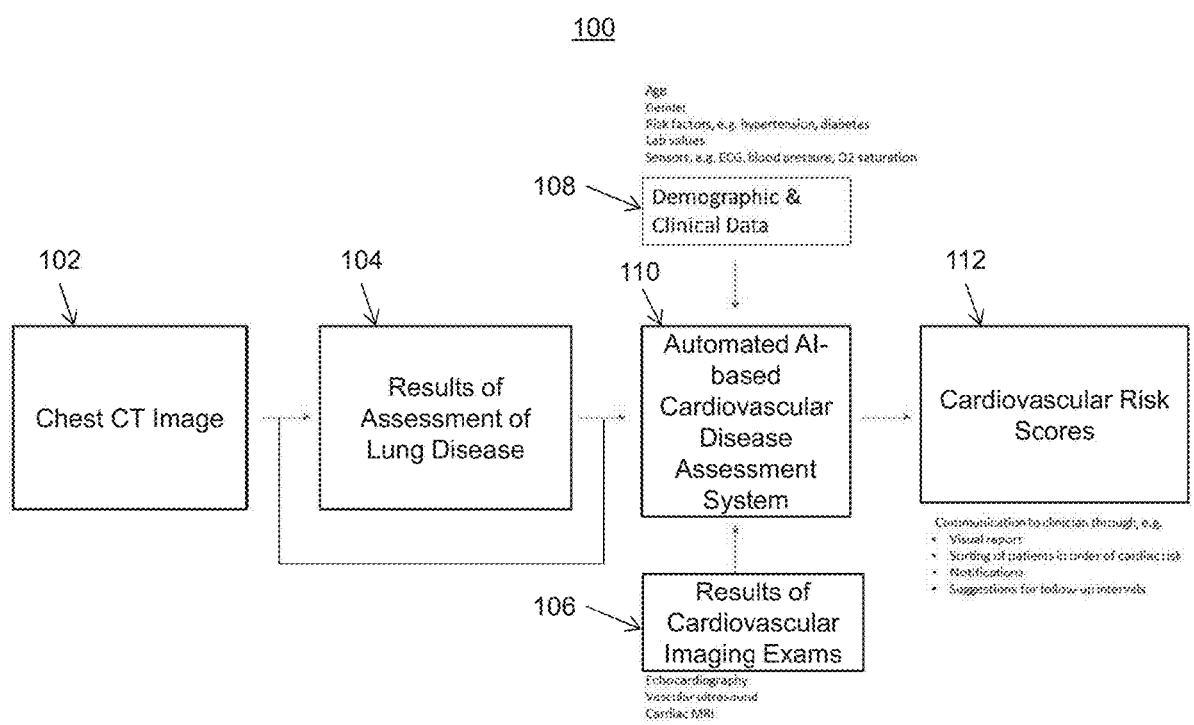
FIG. 1 shows framework for cardiovascular assessment of a patient confirmed as having or suspected of having a lung disease, in accordance with one or more embodiments.
Figure 2:
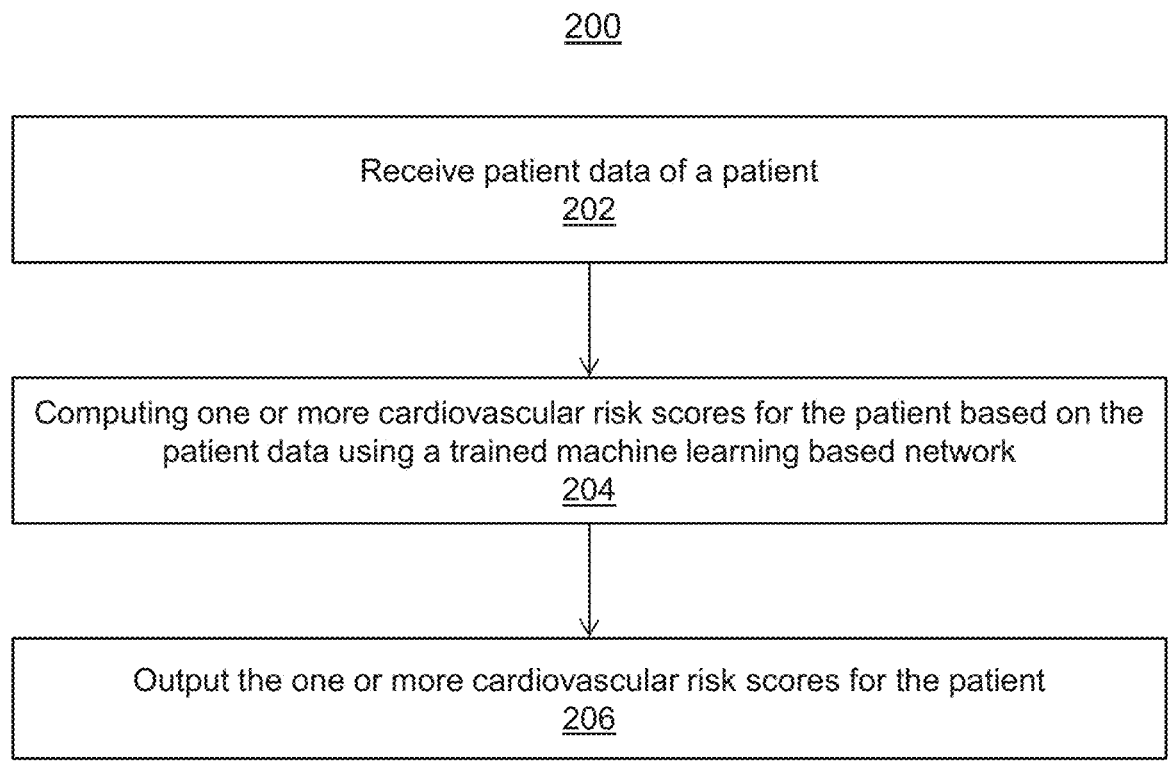
FIG. 2 shows a method for cardiovascular assessment of a patient confirmed as having or suspected of having a lung disease, in accordance with one or more embodiments.

FIG. 1 shows a framework 100 for cardiovascular assessment of a patient confirmed as having or suspected of having a lung disease, in accordance with one or more embodiments. FIG. 2 shows a method 200 for cardiovascular assessment of a patient confirmed as having or suspected of having a lung disease, in accordance with one or more embodiments. FIG. 1 and FIG. 2 will be described together. The steps of method 200 may be performed by one or more computing devices, such as, e.g., computer 502 of FIG. 5.

At step 202, patient data of a patient is received. The patient may be confirmed as having or suspected of having a lung disease. In one embodiment, the lung disease is COVID-19. However, the lung disease may include any disease associated with the lungs of the patient, such as, e.g., other types of viral pneumonia (e.g., SARS (severe acute respiratory syndrome), MERS (Middle East respiratory syndrome), etc.), bacterial pneumonia, fungal pneumonia, mycoplasma pneumonia, and other types of pneumonia and other types of diseases.

In one embodiment, the patient data includes one or more input medical images of the chest (including the lungs and the heart) of the patient. The input medical images may depict abnormality patterns associated with the lung disease. For example, where the lung disease is COVID-19, the input medical images may show opacities such as, e.g., GGO (ground glass opacity), consolidation, crazy-paving pattern, atelectasis, interlobular septal thickening, pleural effusions, bronchiectasis, etc.

In one embodiment, the input medical images are CT input medical images. For example, the input medical images may be chest CT image 102 in framework 100 of FIG. 1. However, the input medical images may be of any suitable modality, such as, e.g., MRI (magnetic resonance imaging), US (ultrasound), x-ray, or any other modality or combination of modalities. The input medical images may comprise one or more 2D images or 3D volumes. The input medical images may be received directly from an image acquisition device, such as, e.g., a CT scanner, as the input medical images are acquired, or can be received by loading previously acquired input medical images from a storage or memory of a computer system or receiving the input medical images from a remote computer system.

In one embodiment, the input medical images are acquired during a clinical workflow for diagnosing or treating the patient for the lung disease. Accordingly, the input medical images may be acquired with or without using a contrast agent, without cardiac gating, with a relatively lower spatial resolution as compared to typical cardiac CT imaging, and with low dose CT imaging. While such images are suitable for assessment of the lung disease, the images are relatively lower quality images as compared to typical medical images acquired for the purpose of assessing cardiovascular disease.

In one embodiment, the patient data includes results of an assessment of the lung disease performed based on the input medical images. For example, the results of the assessment of the lung disease may be results of assessment of lung disease 104 in framework 100 of FIG. 1. In one embodiment, the assessment of the lung disease is a quantitative assessment of the lung disease performed on the input medical images using a machine learning based network. The results of the quantitative assessment may include metrics quantifying the lung disease. For example, where the lung disease is COVID-19, the quantitative assessment may quantify abnormality patterns associated with COVID-19. Exemplary metrics include a PO (percent of opacity) metric calculated as the total percent volume of the lungs that is affected by the disease and a LSS (lung severity score) metric calculated as a cumulative measure of the extent of lung involvement in the disease across each lobe of the lungs. Other metrics are also contemplated. In one embodiment, the assessment of the lung disease is a qualitative assessment of the lung disease performed by a clinician or other user.

In one embodiment, the patient data includes results of cardiovascular imaging exams. For example, the results of cardiovascular imaging exams may be results of cardiovascular imaging exams 106 in framework 100 of FIG. 1. The cardiovascular imaging exam may be based on any suitable modality or combination of modalities. Exemplary cardiovascular imaging exams include echocardiography, vascular ultrasound, cardiac MRI, cardiac CT, cardiac PET, or any other cardiovascular imaging exam.

In one embodiment, the patient data includes demographic and clinical data of the patient. For example, the demographic and clinical data may be demographic and clinical data 108 in framework 100 of FIG. 1. The demographic and clinical data may include any data relating to the patient, such as, e.g., age, gender, clinical history, genetic and family history, risk factors (e.g., hypertension, diabetes, etc.), lab values, etc.

In one embodiment, the demographic and clinical data includes sensor data of physiological measurements of the patient. The sensor data may include, e.g., ECG (electrocardiogram) data, EEG (electroencephalography) data, blood pressure data, O2 (oxygen) saturation, blood pH, glucose levels, etc. The sensor data may be acquired from sensors and medical equipment, including non-medical grade sensor devices. Exemplary sensors include a blood pressure meter, heart rate sensor, ECG monitor, pulse oximeter, O2 saturation sensor, sweat sensors, smart watches and wearable sensors, etc. The sensor data may be continuously acquired or periodically acquired at predetermined intervals.

At step 204, one or more cardiovascular risk scores are computed for the patient based on the patient data using a trained machine learning based network. The cardiovascular risk scores represent an assessment of risk or injury relating to the heart or vessels of the patient. In one example, cardiovascular risk scores 112 are computed using automated AI (artificial intelligence)-based cardiovascular disease assessment system 110 in framework 100 of FIG. 1. In one embodiment, the trained machine learning based network is a deep learning based network, however any other suitable machine learning based network may be employed. In one embodiment, the cardiovascular risk scores are based on multiple cardiovascular findings independently determined by different respective machine learning networks. The trained machine learning based network is trained to compute that cardiovascular risk scores during a prior offline or training stage using a training dataset and, once trained, applied at step 204 during an online or inference stage.

In one embodiment, the cardiovascular risk scores of the patient represents a quantification of cardiovascular risk of the patient. For example, the cardiovascular risk scores may be a quantification of an amount of calcium in the coronary arteries (total calcium or calcium in each branch), a quantification of a calcium load in the aorta (e.g., the aortic root, thoracic aorta, or aortic valve leaflets), or a quantification of the size of the aorta and pulmonary artery. In another example, the cardiovascular risk scores may be a quantification of epicardial fat, paracardial fat, or epicardial adipose tissue. In another example, the cardiovascular risk scores may be a quantification of myocardial fat (infiltration).

In one embodiment, a cardiovascular assessment of the patient is also determined based on the patient data using the trained machine learning based network. The cardiovascular assessment of the patient may comprise an automatic extraction of various anatomical structures (e.g., cardiovascular structures such as pericardium, heart chambers, aorta, pulmonary artery, etc.) from the input medical images. In one embodiment, the cardiovascular assessment of the patient comprises imaging biomarkers identified in the input medical images.

In one embodiment, the cardiovascular assessment of the patient comprises cardiovascular-specific imaging features extracted from the input medical images by the trained machine learning based network. The extracted imaging features may be combined with other patient data for a more comprehensive assessment. For example, the extracted imaging features may be combined with cardiovascular disease imaging biomarkers obtained via ultrasound from other vascular territories, such as, e.g., carotids, aorta, and the ileo-femoral region.

In one embodiment, the cardiovascular assessment of the patient comprises a recommended course of action for clinical decision support. For example, the recommended course of action may be a suggested duration for following up with the patient.

In one embodiment, the cardiovascular risk scores for the patient comprises a combination metric representing an assessment of the cardiovascular disease of the patient, as well as the lung disease of the patient. The combination metric may be computed based on the imaging biomarkers in the input medical image combined with other patient data of the patient. In one example, the combination metric is an assessment of the overall cardiopulmonary system, including the lungs and the heart of the patient, representing the extent, severity, and risk of both the lung disease and cardiovascular disease. In another example, the combination metric may be the assessment of the lungs normalized in the context of the cardiovascular assessment (e.g., the quantification of the cardiovascular risk). In another example, the combination metric may represent the cardiovascular assessment (e.g., the quantification of the cardiovascular risk) quantified in the context of the assessment of the lung disease. For example, the quantification of the cardiovascular risk may be normalized with respect to an amount of infection in the lungs or a lung perfusion. Other metrics may also be employed that do not directly relate to cardiovascular disease.

At step 206, the cardiovascular risk scores and/or the cardiovascular assessment of the patient are output. For example, the cardiovascular risk scores and/or the cardiovascular assessment can be output by displaying the cardiovascular risk scores and/or the cardiovascular assessment on a display device of a computer system, storing the cardiovascular risk scores and/or the cardiovascular assessment on a memory or storage of a computer system, or by transmitting the cardiovascular risk scores and/or the cardiovascular assessment to a remote computer system.

In one embodiment, the cardiovascular risk scores and/or the cardiovascular assessment may be output as a visual report highlighting various sources of cardiac risk (e.g., coronary calcium, epicardial fat, enlargement of great vessels, etc.). The cardiovascular risk scores and/or the cardiovascular assessment for the patient may be displayed in the visual report along with cardiovascular risk scores and/or the cardiovascular assessments for other patients, where the patients are sorted (on demand or automatically) within the visual report based on cardiovascular risk. In one embodiment, a clinician (or other user) may be receive a notification (e.g., an email, text or chat message, or an application based notification) indicating that the cardiovascular risk scores and/or the cardiovascular assessment are complete. The clinical may interact with (e.g., select) the notification to view the cardiovascular risk scores and/or the cardiovascular assessment.

In one embodiment, the cardiovascular risk scores and/or the cardiovascular assessment may be utilized by a clinical for patient management. For example, the clinician may order additional tests, change therapies, manage clinical resources, etc. based on the cardiovascular risk scores and/or the cardiovascular assessment.

In one embodiment, the patient data (including both clinical and non-clinical sources of patient data) may be used in the context of the cardiovascular risk scores and/or the cardiovascular assessment to identify signs of cardiac distress. For example, the patient data may be sensor data from one or more sensors, such as an ECG monitor, blood pressure, sensor, O2 saturation sensor, smart watch, sweat sensor, laboratory testing data (e.g., troponin levels, blood glucose levels, cholesterol, etc.), or any other sensor. The sensor data, in combination with patient data, may be continuously received and used to build a continuously evolving model of the physiology of the patient. The model may be used to monitor the patient for sudden changes indicative of cardiac injury or stress based on the continuously received sensor data and the cardiovascular risk scores and/or the cardiovascular assessment. Where such indications of cardiac injury or stress are detected, a notification may be transmitted to the clinician for further assessment of the patient.

Advantageously, the cardiovascular risk scores and/or the cardiovascular assessment of a patient in accordance with embodiments described herein assist clinicians in patient management decisions and patient stratification. The cardiovascular risk scores and/or the cardiovascular assessment are determined using patient data acquired in the clinical workflow for diagnosing or treating the lung disease and therefore requires minimal time from clinicians, which is particularly important for clinicians treating patients with COVID-19. Further, the cardiovascular risk scores and/or the cardiovascular assessment is determined based on a combination of various patient data and thus, the accuracy of specific patient data is not critical for determining the cardiovascular assessment.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, embodiments described herein are described with respect to methods and systems for cardiovascular assessment of patients suspected of having COVID-19 using a trained machine learning based network, as well as with respect to methods and systems for training a machine learning based network for cardiovascular assessment of patients suspected of having COVID-19. Features, advantages or alternative embodiments herein can be assigned to the other claimed objects and vice versa. In other words, claims for methods and systems for training a machine learning based generator network can be improved with features described or claimed in context of the methods and systems for utilizing a trained machine learning based generator network, and vice versa.

In particular, the trained machine learning based network of the methods and systems for cardiovascular assessment of patients suspected of having COVID-19 can be adapted by the methods and systems for training the machine learning based network for cardiovascular assessment of patients suspected of having COVID-19. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 3:
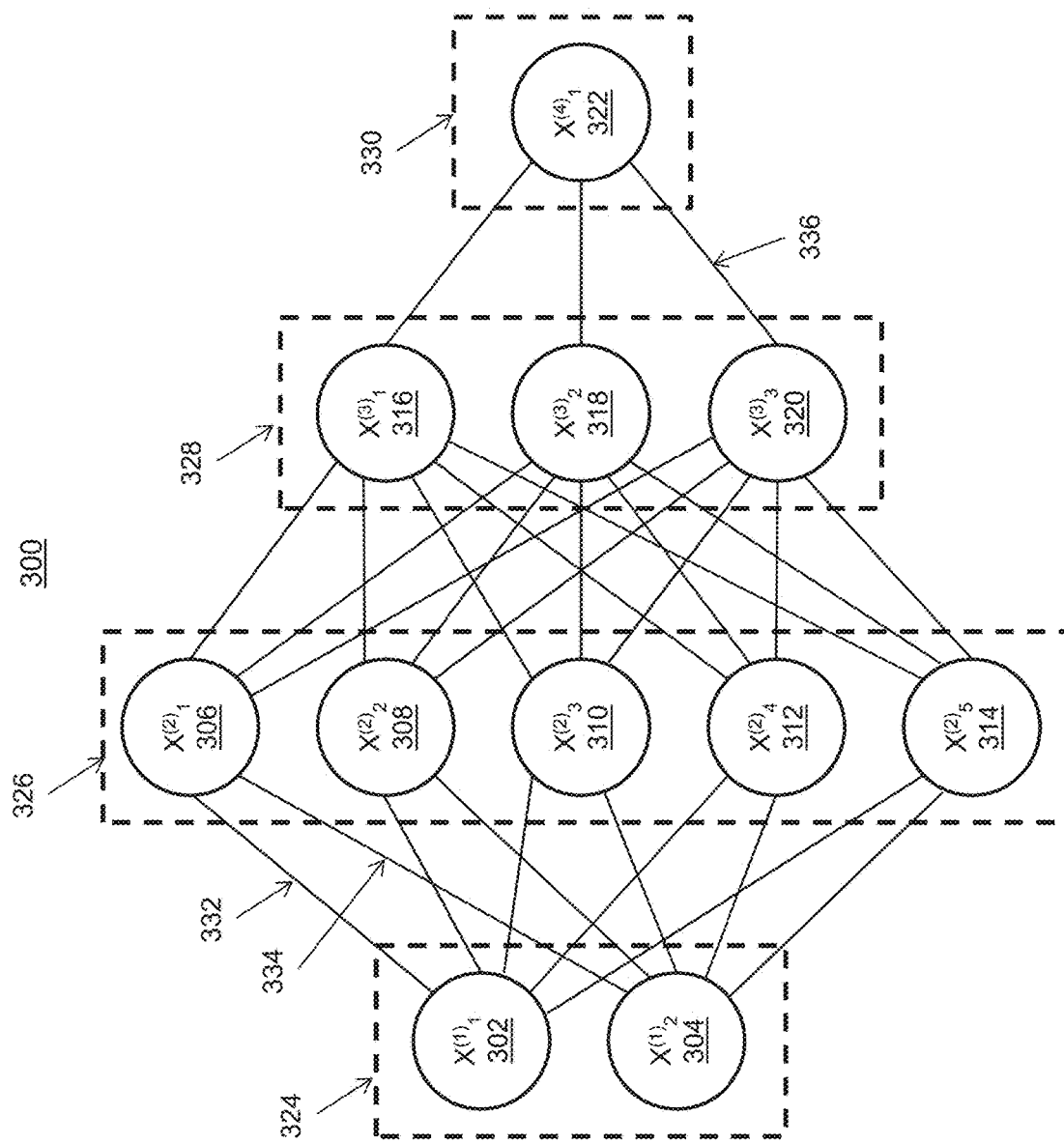
FIG. 3 shows an exemplary artificial neural network that may be used to implement one or more embodiments described herein.

FIG. 3 shows an embodiment of an artificial neural network 300, in accordance with one or more embodiments. Alternative terms for "artificial neural network" are "neural network", "artificial neural net" or "neural net". Machine learning networks described herein, such as, e.g., the automated AI-based cardiovascular disease assessment system 110 of FIG. 1 and the machine learning based network applied at step 204 of FIG. 2, may be implemented using artificial neural network 300.

The artificial neural network 300 comprises nodes 302-322 and edges 332, 334, . . . , 336, wherein each edge 332, 334, . . . , 336 is a directed connection from a first node 302-322 to a second node 302-322. In general, the first node 302-322 and the second node 302-322 are different nodes 302-322, it is also possible that the first node 302-322 and the second node 302-322 are identical. For example, in FIG. 3, the edge 332 is a directed connection from the node 302 to the node 306, and the edge 334 is a directed connection from the node 304 to the node 306. An edge 332, 334, . . . , 336 from a first node 302-322 to a second node 302-322 is also denoted as "ingoing edge" for the second node 302-322 and as "outgoing edge" for the first node 302-322.

In this embodiment, the nodes 302-322 of the artificial neural network 300 can be arranged in layers 324-330, wherein the layers can comprise an intrinsic order introduced by the edges 332, 334, . . . , 336 between the nodes 302-322. In particular, edges 332, 334, . . . , 336 can exist only between neighboring layers of nodes. In the embodiment shown in FIG. 3, there is an input layer 324 comprising only nodes 302 and 304 without an incoming edge, an output layer 330 comprising only node 322 without outgoing edges, and hidden layers 326, 328 in-between the input layer 324 and the output layer 330. In general, the number of hidden layers 326, 328 can be chosen arbitrarily. The number of nodes 302 and 304 within the input layer 324 usually relates to the number of input values of the neural network 300, and the number of nodes 322 within the output layer 330 usually relates to the number of output values of the neural network 300.

In particular, a (real) number can be assigned as a value to every node 302-322 of the neural network 300. Here, $x^{(n)}_i$ denotes the value of the i-th node 302-322 of the n-th layer 324-330. The values of the nodes 302-322 of the input layer 324 are equivalent to the input values of the neural network 300, the value of the node 322 of the output layer 330 is equivalent to the output value of the neural network 300. Furthermore, each edge 332, 334, . . . , 336 can comprise a weight being a real number, in particular, the weight is a real number within the interval [−1, 1] or within the interval [0, 1]. Here, $w^{(m,n)}_{i,j}$ denotes the weight of the edge between the i-th node 302-322 of the m-th layer 324-330 and the j-th node 302-322 of the n-th layer 324-330. Furthermore, the abbreviation $w^{(n)}_{i,j}$ is defined for the weight $w^{(n,n+1)}_{i,j}$.

In particular, to calculate the output values of the neural network 300, the input values are propagated through the neural network. In particular, the values of the nodes 302-322 of the (n+1)-th layer 324-330 can be calculated based on the values of the nodes 302-322 of the n-th layer 324-330 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions The transfer function is mainly used for normalization purposes.

In particular, the values are propagated layer-wise through the neural network, wherein values of the input layer 324 are given by the input of the neural network 300, wherein values of the first hidden layer 326 can be calculated based on the values of the input layer 324 of the neural network, wherein values of the second hidden layer 328 can be calculated based in the values of the first hidden layer 326, etc.

In order to set the values $w^{(m,n)}_{i,j}$ for the edges, the neural network 300 has to be trained using training data. In particular, training data comprises training input data and training output data (denoted as $t_i$). For a training step, the neural network 300 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 300 (backpropagation algorithm). In particular, the weights are changed according to $$w'^{(n)}_{i,j} = w^{(n)}_{i,j} - \gamma \cdot \delta^{(n)}_j \cdot x^{(n)}_i$$

wherein γ is a learning rate, and the numbers $\delta^{(n)}_j$ can be recursively calculated as $$\delta^{(n)}_j = (\Sigma_k \delta^{(n+1)}_k \cdot w^{(n+1)}_{j,k}) \cdot f'(\Sigma_i x^{(n)}_i \cdot w^{(n)}_{i,j})$$

based on $\delta^{(n+1)}_j$, if the (n+1)-th layer is not the output layer, and $$\delta^{(n)}_j = (x^{(n+1)}_k - t^{(n+1)}_j) \cdot f'(\Sigma_i x^{(n)}_i \cdot w^{(n)}_{i,j})$$

if the (n+1)-th layer is the output layer 330, wherein f' is the first derivative of the activation function, and $y^{(n+1)}_j$ is the comparison training value for the j-th node of the output layer 330.

Figure 4:
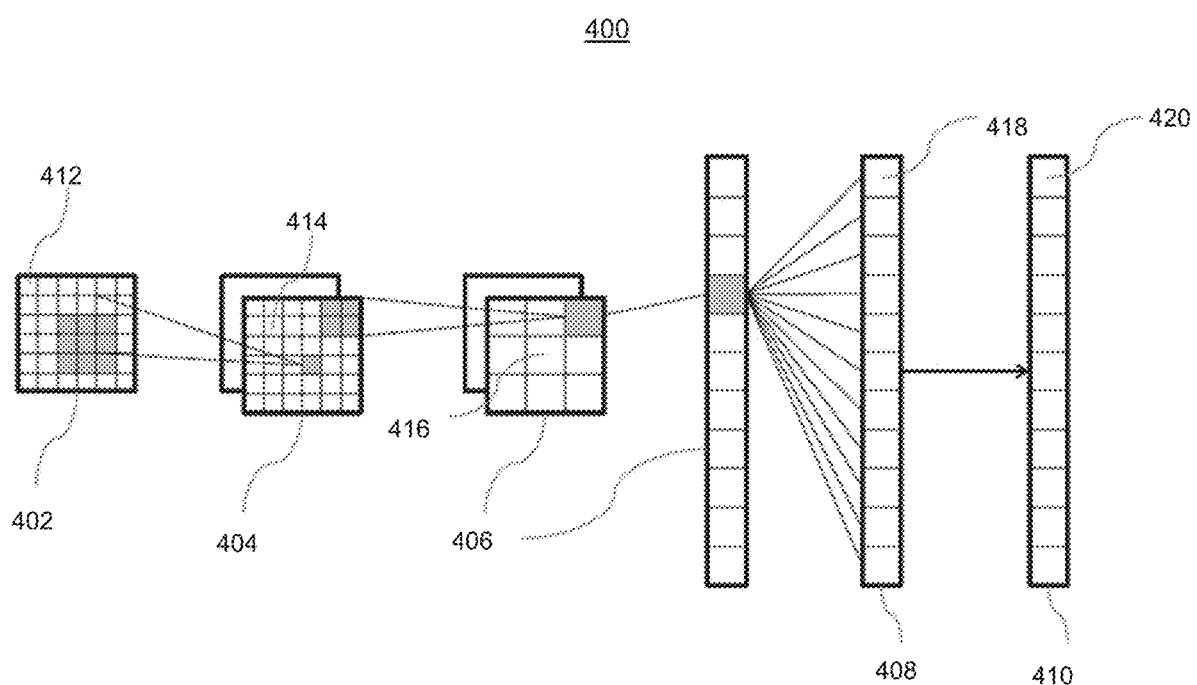
FIG. 4 shows a convolutional neural network that may be used to implement one or more embodiments described herein.

FIG. 4 shows a convolutional neural network 400, in accordance with one or more embodiments. Machine learning networks described herein, such as, e.g., the automated AI-based cardiovascular disease assessment system 110 of FIG. 1 and the machine learning based network applied at step 204 of FIG. 2, may be implemented using convolutional neural network 400.

In the embodiment shown in FIG. 4, the convolutional neural network comprises 400 an input layer 402, a convolutional layer 404, a pooling layer 406, a fully connected layer 408, and an output layer 410. Alternatively, the convolutional neural network 400 can comprise several convolutional layers 404, several pooling layers 406, and several fully connected layers 408, as well as other types of layers. The order of the layers can be chosen arbitrarily, usually fully connected layers 408 are used as the last layers before the output layer 410.

In particular, within a convolutional neural network 400, the nodes 412-420 of one layer 402-410 can be considered to be arranged as a d-dimensional matrix or as a d-dimensional image. In particular, in the two-dimensional case the value of the node 412-420 indexed with i and j in the n-th layer 402-410 can be denoted as $x^{(n)}_{[i,j]}$. However, the arrangement of the nodes 412-420 of one layer 402-410 does not have an effect on the calculations executed within the convolutional neural network 400 as such, since these are given solely by the structure and the weights of the edges.

In particular, a convolutional layer 404 is characterized by the structure and the weights of the incoming edges forming a convolution operation based on a certain number of kernels. In particular, the structure and the weights of the incoming edges are chosen such that the values $x^{(n)}_k$ of the nodes 414 of the convolutional layer 404 are calculated as a convolution $x^{(n)}_k = K_k * x^{(n-1)}$ based on the values $x^{(n-1)}$ of the nodes 412 of the preceding layer 402, where the convolution * is defined in the two-dimensional case as $$x^{(n)}_k[i,j] = (K_k * x^{(n-1)})[i,j] = \Sigma_{i'} \Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 412-418 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 412-420 in the respective layer 402-410. In particular, for a convolutional layer 404, the number of nodes 414 in the convolutional layer is equivalent to the number of nodes 412 in the preceding layer 402 multiplied with the number of kernels.

If the nodes 412 of the preceding layer 402 are arranged as a d-dimensional matrix, using a plurality of kernels can be interpreted as adding a further dimension (denoted as "depth" dimension), so that the nodes 414 of the convolutional layer 414 are arranged as a (d+1)-dimensional matrix. If the nodes 412 of the preceding layer 402 are already arranged as a (d+1)-dimensional matrix comprising a depth dimension, using a plurality of kernels can be interpreted as expanding along the depth dimension, so that the nodes 414 of the convolutional layer 404 are arranged also as a (d+1)-dimensional matrix, wherein the size of the (d+1)-dimensional matrix with respect to the depth dimension is by a factor of the number of kernels larger than in the preceding layer 402.

The advantage of using convolutional layers 404 is that spatially local correlation of the input data can exploited by enforcing a local connectivity pattern between nodes of adjacent layers, in particular by each node being connected to only a small region of the nodes of the preceding layer.

In embodiment shown in FIG. 4, the input layer 402 comprises 36 nodes 412, arranged as a two-dimensional 6×6 matrix. The convolutional layer 404 comprises 72 nodes 414, arranged as two two-dimensional 6×6 matrices, each of the two matrices being the result of a convolution of the values of the input layer with a kernel. Equivalently, the nodes 414 of the convolutional layer 404 can be interpreted as arranges as a three-dimensional 6×6×2 matrix, wherein the last dimension is the depth dimension.

A pooling layer 406 can be characterized by the structure and the weights of the incoming edges and the activation function of its nodes 416 forming a pooling operation based on a non-linear pooling function f. For example, in the two dimensional case the values $x^{(n)}$ of the nodes 416 of the pooling layer 406 can be calculated based on the values $x^{(n-1)}$ of the nodes 414 of the preceding layer 404 as $$x^{(n)}[i,j] = f(x^{(n-1)}[id_1,jd_2], \ldots, x^{(n-1)}[id_1+d_1-1, jd_2+d_2-1])$$

In other words, by using a pooling layer 406, the number of nodes 414, 416 can be reduced, by replacing a number d1·d2 of neighboring nodes 414 in the preceding layer 404 with a single node 416 being calculated as a function of the values of said number of neighboring nodes in the pooling layer. In particular, the pooling function f can be the max-function, the average or the L2-Norm. In particular, for a pooling layer 406 the weights of the incoming edges are fixed and are not modified by training.

The advantage of using a pooling layer 406 is that the number of nodes 414, 416 and the number of parameters is reduced. This leads to the amount of computation in the network being reduced and to a control of overfitting.

In the embodiment shown in FIG. 4, the pooling layer 406 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 408 can be characterized by the fact that a majority, in particular, all edges between nodes 416 of the previous layer 406 and the nodes 418 of the fully-connected layer 408 are present, and wherein the weight of each of the edges can be adjusted individually.

In this embodiment, the nodes 416 of the preceding layer 406 of the fully-connected layer 408 are displayed both as two-dimensional matrices, and additionally as non-related nodes (indicated as a line of nodes, wherein the number of nodes was reduced for a better presentability). In this embodiment, the number of nodes 418 in the fully connected layer 408 is equal to the number of nodes 416 in the preceding layer 406. Alternatively, the number of nodes 416, 418 can differ.

Furthermore, in this embodiment, the values of the nodes 420 of the output layer 410 are determined by applying the Softmax function onto the values of the nodes 418 of the preceding layer 408. By applying the Softmax function, the sum the values of all nodes 420 of the output layer 410 is 1, and all values of all nodes 420 of the output layer are real numbers between 0 and 1.

A convolutional neural network 400 can also comprise a ReLU (rectified linear units) layer. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer. Examples for rectifying functions are $f(x)=\max(0,x)$, the tangent hyperbolics function or the sigmoid function.

In particular, convolutional neural networks 400 can be trained based on the backpropagation algorithm. For preventing overfitting, methods of regularization can be used, e.g. dropout of nodes 412-420, stochastic pooling, use of artificial data, weight decay based on the L1 or the L2 norm, or max norm constraints.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-2. Certain steps or functions of the methods and workflows described herein, including one or more of the steps or functions of FIGS. 1-2, may be performed by a server or by another processor in a network-based cloud-computing system. Certain steps or functions of the methods and workflows described herein, including one or more of the steps of FIGS. 1-2, may be performed by a client computer in a network-based cloud computing system. The steps or functions of the methods and workflows described herein, including one or more of the steps of FIGS. 1-2, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 5:
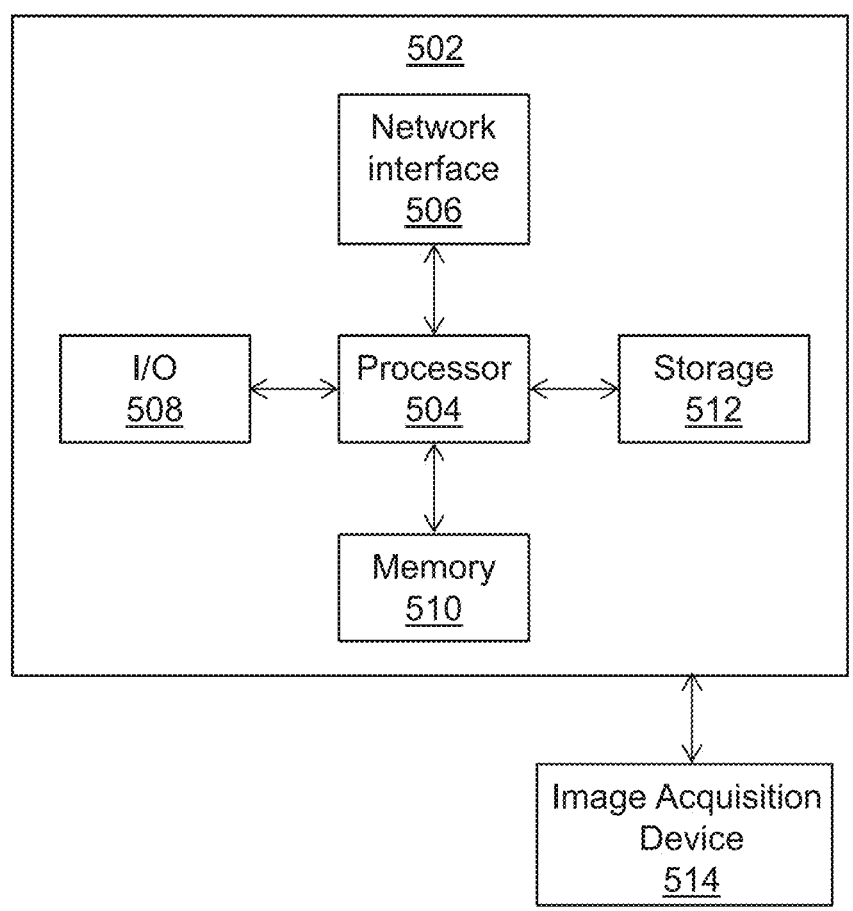
FIG. 5 shows a high-level block diagram of a computer that may be used to implement one or more embodiments described herein.

A high-level block diagram of an example computer 502 that may be used to implement systems, apparatus, and methods described herein is depicted in FIG. 5. Computer 502 includes a processor 504 operatively coupled to a data storage device 512 and a memory 510. Processor 504 controls the overall operation of computer 502 by executing computer program instructions that define such operations. The computer program instructions may be stored in data storage device 512, or other computer readable medium, and loaded into memory 510 when execution of the computer program instructions is desired. Thus, the method and workflow steps or functions of FIGS. 1-2 can be defined by the computer program instructions stored in memory 510 and/or data storage device 512 and controlled by processor 504 executing the computer program instructions. For example, the computer program instructions can be implemented as computer executable code programmed by one skilled in the art to perform the method and workflow steps or functions of FIGS. 1-2. Accordingly, by executing the computer program instructions, the processor 504 executes the method and workflow steps or functions of FIGS. 1-2. Computer 502 may also include one or more network interfaces 506 for communicating with other devices via a network. Computer 502 may also include one or more input/output devices 508 that enable user interaction with computer 502 (e.g., display, keyboard, mouse, speakers, buttons, etc.).

Processor 504 may include both general and special purpose microprocessors, and may be the sole processor or one of multiple processors of computer 502. Processor 504 may include one or more central processing units (CPUs), for example. Processor 504, data storage device 512, and/or memory 510 may include, be supplemented by, or incorporated in, one or more application-specific integrated circuits (ASICs) and/or one or more field programmable gate arrays (FPGAs).

Data storage device 512 and memory 510 each include a tangible non-transitory computer readable storage medium. Data storage device 512, and memory 510, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 508 may include peripherals, such as a printer, scanner, display screen, etc. For example, input/output devices 508 may include a display device such as a cathode ray tube (CRT) or liquid crystal display (LCD) monitor for displaying information to the user, a keyboard, and a pointing device such as a mouse or a trackball by which the user can provide input to computer 502.

An image acquisition device 514 can be connected to the computer 502 to input image data (e.g., medical images) to the computer 502. It is possible to implement the image acquisition device 514 and the computer 502 as one device. It is also possible that the image acquisition device 514 and the computer 502 communicate wirelessly through a network. In a possible embodiment, the computer 502 can be located remotely with respect to the image acquisition device 514.

Any or all of the systems and apparatus discussed herein, including automated AI-based cardiovascular disease assessment system 110 of FIG. 1, the machine learning based network applied at step 204 of FIG. 2, the artificial neural network 300 of FIG. 3, and the convolutional neural network 400 of FIG. 4, may be implemented using one or more computers such as computer 502.

One skilled in the art will recognize that an implementation of an actual computer or computer system may have other structures and may contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer implemented method comprising:
receiving patient data of a patient, the patient data comprising one or more input medical images of a chest of the patient, one or more metrics quantifying abnormality patterns of a lung disease in lungs of the patient determined based on the one or more input medical images, and results of cardiovascular imaging exams; and
computing a combination metric representing an assessment of cardiovascular disease of the patient and an assessment of lung disease of the patient using a trained machine learning based network, the trained machine learning based network computing the combination metric based on the one or more input medical images of the chest of the patient, the one or more metrics quantifying the abnormality patterns of the lung disease in the lungs of the patient, and the results of the cardiovascular imaging exams.

2. The computer implemented method of claim 1, wherein the lung disease is COVID-19 (coronavirus disease 2019).

3. The computer implemented method of claim 1, wherein the one or more input medical images was acquired without a contrast agent.

4. The computer implemented method of claim 1, wherein the one or more input medical images was acquired without cardiac gating.

5. The computer implemented method of claim 1, wherein the patient data further comprises sensor data of physiological measurements of the patient, the method further comprising:
continuously receiving the sensor data; and
monitoring the patient based on the continuously received sensor data and the combination metric.

6. The computer implemented method of claim 1, wherein the patient data further comprises demographic and clinical data of the patient.

7. The computer implemented method of claim 1, wherein the lung disease is a viral pneumonia.

8. The computer implemented method of claim 1, further comprising:
managing the patient based on the combination metric.

9. An apparatus comprising:
means for receiving patient data of a patient, the patient data comprising one or more input medical images of a chest of the patient, one or more metrics quantifying abnormality patterns of a lung disease in lungs of the patient determined based on the one or more input medical images, and results of cardiovascular imaging exams; and
means for computing a combination metric representing an assessment of cardiovascular disease of the patient and an assessment of lung disease of the patient using a trained machine learning based network, the trained machine learning based network computing the combination metric based on the one or more input medical images of the chest of the patient, the one or more metrics quantifying the abnormality patterns of the lung disease in the lungs of the patient, and the results of the cardiovascular imaging exams.

10. The apparatus of claim 9, wherein the lung disease is COVID-19 (coronavirus disease 2019).

11. The apparatus of claim 9, wherein the one or more input medical images was acquired without a contrast agent.

12. The apparatus of claim 9, wherein the one or more input medical images was acquired without cardiac gating.

13. The apparatus of claim 9, wherein the lung disease is a viral pneumonia.

14. A non-transitory computer readable medium storing computer program instructions, the computer program instructions when executed by a processor cause the processor to perform operations comprising:

receiving patient data of a patient, the patient data comprising one or more input medical images of a chest of the patient, one or more metrics quantifying abnormality patterns of a lung disease in lungs of the patient determined based on the one or more input medical images, and results of cardiovascular imaging exams; and computing a combination metric representing an assessment of cardiovascular disease of the patient and an assessment of lung disease of the patient using a trained machine learning based network, the trained machine learning based network computing the combination metric based on the one or more input medical images of the chest of the patient, the one or more metrics quantifying the abnormality patterns of the lung disease in the lungs of the patient, and the results of the cardiovascular imaging exams.

15. The non-transitory computer readable medium of claim 14, wherein the lung disease is COVID-19 (coronavirus disease 2019).

16. The non-transitory computer readable medium of claim 14, wherein the patient data further comprises sensor data of physiological measurements of the patient, the operations further comprising:
  continuously receiving the sensor data; and
  monitoring the patient based on the continuously received sensor data and the combination metric.

17. The non-transitory computer readable medium of claim 14, wherein the patient data further comprises demographic and clinical data of the patient.

18. The non-transitory computer readable medium of claim 14, wherein the lung disease is a viral pneumonia.

* * * * *